US00PP20672P2

(12) United States Plant Patent
Hofmann

(10) Patent No.: US PP20,672 P2
(45) Date of Patent: Jan. 26, 2010

(54) ***MANDEVILLA* PLANT NAMED 'FISRIX HOPINK'**

(50) Latin Name: *Mandevilla sanderi*
Varietal Denomination: Fisrix Hopink

(75) Inventor: Birgit Christa Hofmann, Rüdesheim (DE)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/220,157

(22) Filed: Jul. 22, 2008

(51) Int. Cl.
*A01H 5/00* (2006.01)

(52) U.S. Cl. ..... Plt./232
(58) Field of Classification Search ..... Plt./232
See application file for complete search history.

(56) References Cited

U.S. PATENT DOCUMENTS

PP15,539 P2 * 2/2005 Misato et al. ..... Plt./232

* cited by examiner

*Primary Examiner*—Susan B McCormick Ewoldt
(74) *Attorney, Agent, or Firm*—S. Matthew Edwards

(57) ABSTRACT

A new *Mandevilla* plant named 'Fisrix Hopink,' particularly distinguished by rose red to cherry red colored flowers, early flowering medium green, glossy foliage, broad, ovate leaves, well branching, upright to spreading, moderately tight and bushy, medium to tall sized.

2 Drawing Sheets

Latin name of the genus and species of the plant claimed: *Mandevilla sanderi* (Hemsl.) Woodson.

Varietal denomination: 'Fisrix Hopink'.

BACKGROUND OF THE NEW PLANT

The present invention comprises a new and distinct cultivar of *Mandevilla*, botanically known as *Mandevilla sanderi*, and hereinafter referred to by the variety name 'Fisrix Hopink.'

'Fisrix Hopink' is a product of a planned breeding program. The new cultivar 'Fisrix Hopink' is florferious with flowers of light red to rose red, has deep green, glossy foliage, in combination with fairly upright, bushy plant habit.

'Fisrix Hopink' originated from a hybridization made in the summer of 2003 in Hillscheid, Germany. The female parent is the commercial *Mandevilla* variety offered as 'Sundaville'® Red, 'Moulin Rouge' in France, which is identical to 'Sunmandecrim,' U.S. Plant Pat. No. 15,539, having red flower color, good branching characteristics, and medium green to grass green foliage. The male parent is the commercial *Mandevilla* variety 'Red Riding Hood' (not patented) with purple pink, medium sized flowers, and deep green leaves.

The seeds produced by the hybridization were sown in the fall of 2003. The resulting seedlings (plants) were evaluated in late summer to fall of 2004. 'Fisrix Hopink' was selected as one flowering plant in a greenhouse in Hillscheid, Germany.

The plant has been asexually reproduced for the first time by vegetative cuttings in Hillscheid, Germany in the fall of 2004 and has been reproduced repeatedly by vegetative cuttings in Hillscheid, Germany over a 2–3 year period. Horticultural examination of plants grown from cuttings of the plant initiated in Hillscheid, Germany, in the spring of 2005, and continuing thereafter, has demonstrated that the combination of characteristics as herein disclosed for 'Fisrix Hopink' are firmly fixed and are retained through successive generations of asexual reproduction.

Plant Breeder's Rights for this cultivar were applied for in Europe on Dec. 13, 2006 and in Canada on Jan. 28, 2008. 'Fisrix Hopink' has not been made publicly available more than one year prior to the filing of this application.

DESCRIPTION OF THE PHOTOGRAPHS

This new *Mandevilla* plant is illustrated by the accompanying photographs which show blooms, buds, and foliage of the plant in full color. The colors shown are as true as can be reasonably obtained by conventional photographic procedures.

FIG. 1 is of a 9 month old plant grown in a greenhouse from the fall of 2006 to the early summer of 2007.

FIG. 2 shows mature inflorescence(s) and buds.

DETAILED BOTANICAL DESCRIPTION

The following detailed descriptions set forth the distinctive characteristics of 'Fisrix Hopink.' The data which define these characteristics were collected from asexual reproductions carried out in Hillscheid, Germany. The plant history was taken in early June 2007 on 9 month old plants, planted in late August to early September 2006, pinched once, and grown in 12 cm diameter pots/containers in a glass-covered greenhouse with additional light during the winter months.

Color readings were taken under natural light. Color references are primarily to The R.H.S. Colour Chart of The Royal Horticultural Society of London (R.H.S.) (2001 edition). Texture description details were observed under a magnifying glass.

BRIEF SUMMARY OF INVENTION

The following are the most outstanding and distinguishing characteristics of this new cultivar when grown under normal horticultural practices in Hillscheid, Germany.

1. Rose red to cherry red colored flowers
2. Medium to large sized flowers, early flowering and floriferous
3. Medium to deep green foliage with broad, ovate, glossy leaves
3. Moderately vigorous habit; and good branching characteristics
4. Medium to tall, upright to spreading plant habit, and relatively compact structure

COMPARISON WITH PARENTAL AND COMMERCIAL CULTIVARS

'Fisrix Hopink' differs from the female parent, *Mandevilla* plant 'Sunmandecrim' (U.S. Plant Pat. No. 15,539), in that 'Fisrix Hopink' has a somewhat lighter and more bluish red hue of flower color, while 'Sunmandecrim' has medium red flowers of narrower shape. Additionally, 'Fisrix Hopink' has wider leaves, and plant grow more upright with less tendency to developing vines.

'Fisrix Hopink' differs from the male parent, the commercial *Mandevilla* plant 'Red Riding Hood' (not patented), in that 'Fisrix Hopink' has a deeper and more uniform cherry flower color, while 'Red Riding Hood' has carmine young flowers that become lighter and turn purple-pink with maturing. Additionally, plants of 'Fisrix Hopink' develop more branches than 'Red Riding Hood.'

'Fisrix Hopink' differs from the commercial cultivar 'Scarlet Pimpernell' (U.S. Plant Pat. No. 9,118 under the denomination 'Cerise') in that 'Fisrix Hopink' has larger, especially longer flowers, of a somewhat more bluish red or cherry red overall flower color, and orange throat color, while 'Scarlet Pimpernell/Cerise' has yellow inner surface color. Additionally, 'Fisrix Hopink' has less distinct reddish coloring of leaf veins and petioles and stronger branching.

DESCRIPTION OF THE PLANT

Classification:

*Family*.—Apocynaceae.

*Botanical name*.—*Mandevilla sanderi* (Hemsl.) Woodson.

Parentage:

*Female parent*.—'Sunmandecrim,' a red flowerd *Mandevilla* plant (U.S. Plant Pat. No. 15,539).

*Male parent*.—'Red Riding Hood', a commercial, pink to purple pink flowered *Mandevilla* cultivar (not patented).

Whole plant:

*Form and growth habit*.—Perennial or sub-shrub with herbaceous younger stems and vines, and woody bases, initially upright, later overhanging, vines are developed mainly during winter months or low light conditions; commercially mostly grown as an annual plant.

*Height*.—38–42 cm (from top of soil) for 9 month old plants.

*Width*.—About 30–35 cm for the foliage canopy, about 45–52 cm total width including inflorescenes.

*Time to produce a finished flowering plant*.—4–5 months for a plant in a 12 cm pot in winter to spring cultivation.

*Plant use and outdoor plant performance*.—For flower pot or for larger containers, best with support, or outdoors in a flower bed, good heat and drought tolerance.

*Time to initiate and develop roots*.—About 25 days.

*Root description*.—Fibrous, a little fleshy, and freely branching.

Stems:

*Number of (main) branches*.—8–12.

*Length*.—28–36 cm without the inflorescence (excluding veins).

*Diameter*.—3–4 mm as measured in the middle.

*Internode length*.—Approximately 2.5–3.5 cm.

*Color*.—Grass green RHS 143B–C, no anthocyanin, woody base: color RHS 174C.

*Texture*.—Glabrous, upper portions are smooth, towards base increasingly rougher, muricate and weakly rugose, bark-like.

Leaves:

*Arrangement*.—Usually opposite, partly decussate.

*Shape*.—Broad, ovate to elliptical.

*Apex*.—Cuspidate.

*Base*.—Truncate to weakly rounded.

*Margin*.—Entire.

*Length*.—5.8–6.5 cm.

*Width*.—4.8–5.6 cm.

*Color of young leaves*.—Upper surface: RHS 143B to 143C, grass green Lower surface: RHS 144B, very young leaves with weak infusion of anthocyanin.

*Color of mature (fully expanded) foliage*.—Upper surface: RHS 137B to 137C Lower surface: Approximately intermediate between RHS 143C and RHS 144B.

*Venation*.—

*Type*.—Pinnate.

*Color*.—Upper side RHS 144A, lower side RHS 154A.

*Texture*.—Appears smooth and glabrous, glossy.

Petiole:

*Length*.—1.2–1.5 mm.

*Width*.—2 mm.

*Color*.—Upper sides: especially with young leaves reddish brown, RHS 181 C, later closer to RHS 181 D Lower sides: light green, RHS 145B to 154C.

Flower bud (just before unfolding the petals):

*Shape*.—Elongated, spindle shaped.

*Diameter*.—1.1–1.3 cm.

*Length*.—6.5–7.5 cm.

*Color (at tight bud)*.—Upper part (future petals): deep red, RHS 53B: Lower part: light green, RHS 145B.

Inflorescence:

*Inflorescence type*.—Raceme emerging from the nodes of the stems with the flowers in an alternative arrangement.

*Blooming habit*.—Continuously through the summer months.

*Quantity of inflorescences per plant*.—8–10.

*Lastingness of individual blooms on the plant*.—10 days.

*Fragrance*.—None.

*Number of flowers per inflorescence*.—5–6 in various stages of development.

*Inflorescence length*.—Up to approximately 15 cm (including peduncle).

Peduncle:

*Color*.—Grass green, RHS 143A to 143B.

*Length*.—Approximately 5–6 cm.

*Diameter*.—2–3 mm.

*Texture*.—Glossy, very short sparse hair.

FLower:

*Type*.—Single.

*Shape of corolla*.—Base of the corolla is tube to funnel shaped, upper part is funnel shaped to wide open, star shaped flower 'face'.

*Length* (*depth*).—6–7 cm.

*Width* (*diameter of flower 'face'*).—8–9 cm.

*Diameter of flower throat*.—2.0 cm.

*Color: General tonality*.—Cherry to deep rose-red.

*Color upper surface ('face')*.—RHS 53C to 53D.

*Lower surface*.—RHS 53C to 53D.

*Color funnel inside*.—Orange, RHS 35A.

*Color funnel, outer surface*.—RHS 53D or somewhat lighter.

Petals (lobes): 5.

*Arrangement*.—Lower parts fused and forming the tube, free lobes opening outwards, aspect varying from 45° to nearly right angles, partly overlapping.

*Shape of lobes*.—Roughly ovate to triangular, asymmetric, with the right part of the petal blade much wider than the left one and with distinctly pointed tips.

*Apex*.—Acuminate.

*Base*.—Fused.

*Margin*.—Entire.

*Texture*.—Smooth.

*Length* (*from the corolla opening*).—40–45 mm.

*Width*.—35–38 mm.

Calyx: 5 sepals, small, closely attached to the base of the flower.

*Shape*.—Ligulate.

*Color*.—Pale green, RHS 145A, to brownish pink, at the tip, RHS 181C, margins semi-transparent.

*Length*.—5–6 mm.

*Width*.—1 mm at the base (maximum).

*Apex*.—Acute, appears almost spine like, yet soft.

*Base*.—Fused.

*Texture*.—Glabrous.

Pedicels:

*Color*.—RHS 145A, page green, slight infusion of anthocyanin (brownish pink color) may occur.

*Length*.—1.8–3.0 cm.

*Diameter*.—2 mm.

*Texture*.—Glabrous, smooth.

Reproductive organs:

*Stamens*.—5, emerge from the base of the corolla, arranged around the style, connivent.

*Anthers*.—2 thecae, surface color: RHS 20C (light yellow-orange), about 10 mm in length.

*Filaments*.—Fused with the base of the flower

*Pollen amount*.—Moderate.

*Pollen color*.—RHS 11D.

*Pistils*.—One per flower, stigma with 5 lobes.

*Length*.—2.0–2.5 cm.

*Stigma color*.—RHS 150D.

*Style color*.—RHS 150B.

Fruit and seed set: Spontaneous seed set has not been observed to date.

Disease/pest resistance: Disease resistance and/or susceptibility has not been observed to date.

What is claimed is:

1. A new and distinct variety of *Mandevilla* plant named 'Fisrix Hopink,' substantially as illustrated and described herein.

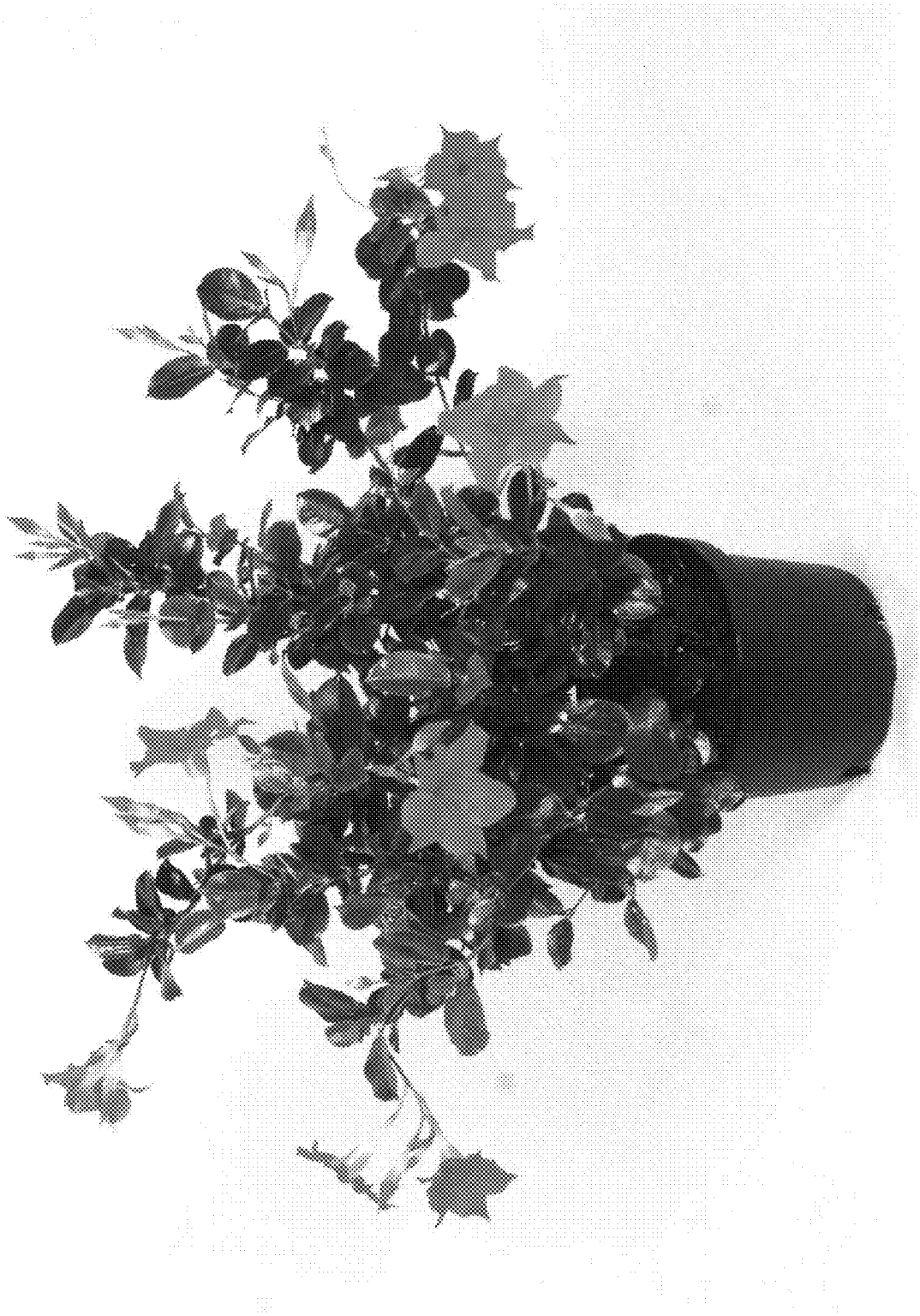

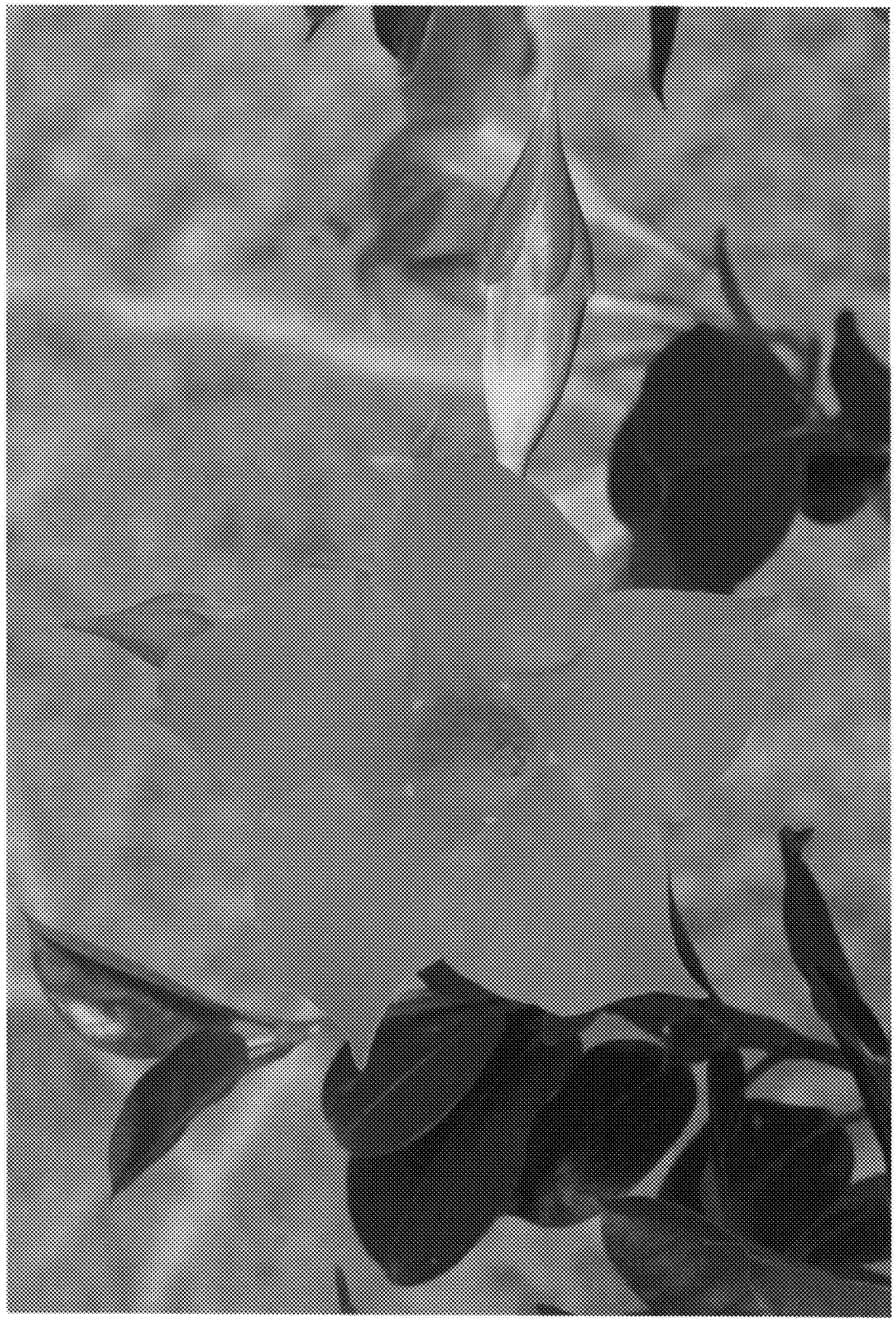

* * * * *